United States Patent
Plank

Patent Number: 5,926,853
Date of Patent: Jul. 27, 1999

[54] COMFORT SUPPORT FOR WOMEN

[76] Inventor: Gloria H. Plank, 906 Southern Pine Ln., Sarasota, Fla. 34243

[21] Appl. No.: 09/151,647

[22] Filed: Sep. 10, 1998

[51] Int. Cl.[6] .................................................. A41B 9/00
[52] U.S. Cl. .................................. 2/406; 450/115; 2/400
[58] Field of Search ............................... 2/401, 402, 403, 2/406, 409, 44, 92, 400; 604/389, 391, 392, 393, 396, 397, 398, 401; 602/67–72; 128/873–876, 883–885, 158, 159, 96.1, 845; 450/131, 133, 132, 114, 155, 151, 115, 116, 117, 119–121, 130, 154

[56] References Cited

U.S. PATENT DOCUMENTS

| | | | |
|---|---|---|---|
| 1,920,648 | 8/1933 | Lane ........................................ | 128/159 X |
| 1,936,336 | 11/1933 | Montmarquet . | |
| 1,989,686 | 2/1935 | Deutsch ................................... | 2/406 |
| 2,248,204 | 7/1941 | Snider ......................................... | 2/44 |
| 2,355,740 | 8/1944 | McNees ................................ | 128/159 X |
| 2,401,457 | 6/1946 | Bryant . | |
| 2,545,224 | 3/1951 | Butler ...................................... | 602/67 X |
| 2,891,545 | 6/1959 | Teague .................................... | 602/70 X |
| 3,029,814 | 4/1962 | Kravitz . | |
| 5,143,092 | 9/1992 | Flowers . | |
| 5,212,839 | 5/1993 | Sliman et al. . | |
| 5,368,050 | 11/1994 | Donelan .................................. | 2/400 X |
| 5,388,275 | 2/1995 | Oram . | |
| 5,528,775 | 6/1996 | Marenda . | |

*Primary Examiner*—Gloria Hale

[57] ABSTRACT

The invention relates to a support garment mainly to be worn by women who experienced weakened muscles or a fallen uterus. The support garment consists of an adjustable or elastic waistband with a support band separably attached to the waistband which is placed between the legs of the wearer. At approximately midway of the support band, a support package is located so as to be located between the legs of a wearer. The support package consists of a semi-rigid but flexible open grid panel of plastic material which is in contact with an upper surface of the support band. A sheet of soft padding is wrapped around the panel and the support band so as to form a package.

7 Claims, 4 Drawing Sheets

COMFORT SUPPORT FOR WOMEN

BACKGROUND OF THE INVENTION

This invention relates to a support system for women. It is not intended to diagnose, treat, cure, or prevent any diseases.

The invention helps relieve pressure from sagging muscles as a result of exercising such a walking, jogging, jumping, lifting, the use of fitness machines etc. Especially for women, any over-exercising can result in a fallen uterus leading to a very uncomfortable condition. The comfort support is designed to function as a "holdback" for the uterus and to prevent it from falling further. It is also designed for the relief of fatigue and discomfort.

Muscles sag and lose elasticity as one ages. With this support, one now has the opportunity to exercise, tone, tighten and strengthen the muscles and to promote better posture.

OBJECTS OF THE INVENTION

It is an object of the invention to provide a garment which is simple in its construction and is comfortable to wear and not detectable when worn under clothing. The garment consists of an elastic band constructed of several stretch panels. One of the bands is to be placed between the legs similar to a sanitary belt but not like it. The band between the legs has a somewhat rigid but flexible panel that is in contact with sagging muscles and/or a fallen uterus. The somewhat rigid but flexible panel may be surrounded by absorbing padding for sanitary reasons.

The absorbent padding may be constructed in such a manner so that it can be removed from the support band between the legs. The support panel could be square or take other shapes so that it is comfortable to wear between the legs and to prevent any chafing.

DISCUSSION OF THE PRIOR ART

U.S. Pat. No. 1,936,336 to Montmarquet shows an athletic girdle for women which is mainly designed to support the abdominal cavity to assure freedom from injury.

U.S. Pat. No. 2,401,457 to Bryant is a lady's under garment which is directed to a panty to render it more comfortable when worn.

U.S. Pat. No. 3,029,814 to Kravitz shows a supporting garment for the groin and abdominal areas. It is primarily adapted to be worn by men but is also usable by women.

U.S. Pat. No. 2,891,545 to Teague is directed to a T-binder mostly used in hospitals in the maternity Ward and has its purpose to hold sanitary napkins in place during the immediate postnatal period.

U.S. Pat. No. 5,143,092 to Flowers is designated as a flexible abdominal flattener for the female's abdomen and has no indication as being usable as a sagging muscle supporter.

U.S. Pat. No. 5,221,839 to Sliman et al is a holder for a diaper for a person being in a body cast. There is no indication that this garment could be used to relieve pressure from sagging muscles.

U.S. Pat. No. 5,388,275 to Oram is designed as protective wear for a female water skier. A protective flexible panel is worn in a pocket of a trunk of a swim suit and is designed to protect the female skiers against forceful contact with water especially in the crotch area during a spill or a so called "wipe-out".

U.S. Pat. No. 5,528,775 to Marenda is a support garment designed for controlling abdominal bulge as a result of an overweight condition or a bloating related to the menstrual cycle.

All of the above cited patents to not relate at all to the objects of this invention and that is to support the sagging of muscles and, when necessary, to support a fallen uterus when conditions warrant the same.

DETAILED DESCRIPTION OF THE DRAWINGS

Figure 1:
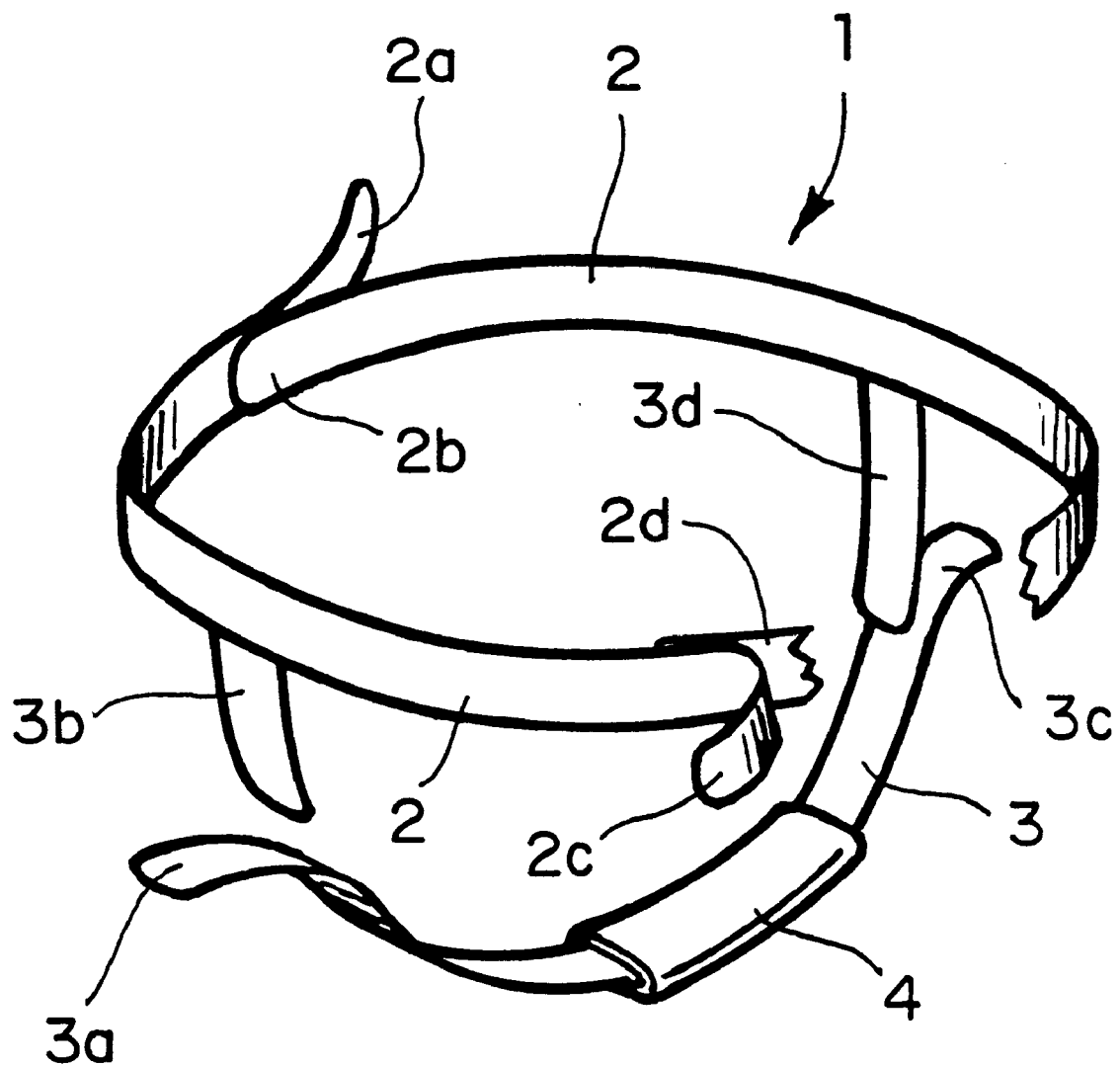
FIG. 1 is a perspective view of the overall support garment.

FIG. 1 shows a perspective view of the support garment wherein the waistband 2 is shown in two parts. The reason for this is to gain an adjustability of the waistband 2 even though the waistband 2 could be elastic by itself. Under certain circumstances the waistband could be non-elastic. This depends largely on the body build of the person wearing the same. To this end, the waistband 2 may have two areas of adjustability. At one location there is a well known hook 2a and loop 2b fastener provided and at another location there is the well known hook 2c and loop 2d fastener. It should be clear that the waistband could have a hook and loop fastener at only one location.

The support garment 1 also has a support band 3 which will be located between the legs. The support band 3 is removably attached to the waistband 2 by hook 3a and loop 3b material at a front location and hook 3c and loop 3d material at a rear location. In this manner the support band 3 can be removed from the waistband for sanitary reasons and for changing to another band having a different contour as will be explained below. At about the middle of the support band there is located a support package 4. When the garment is worn the support package 4 is in contact with and supports the weakened muscles between the legs of the wearer including a fallen uterus.

Figure 2:
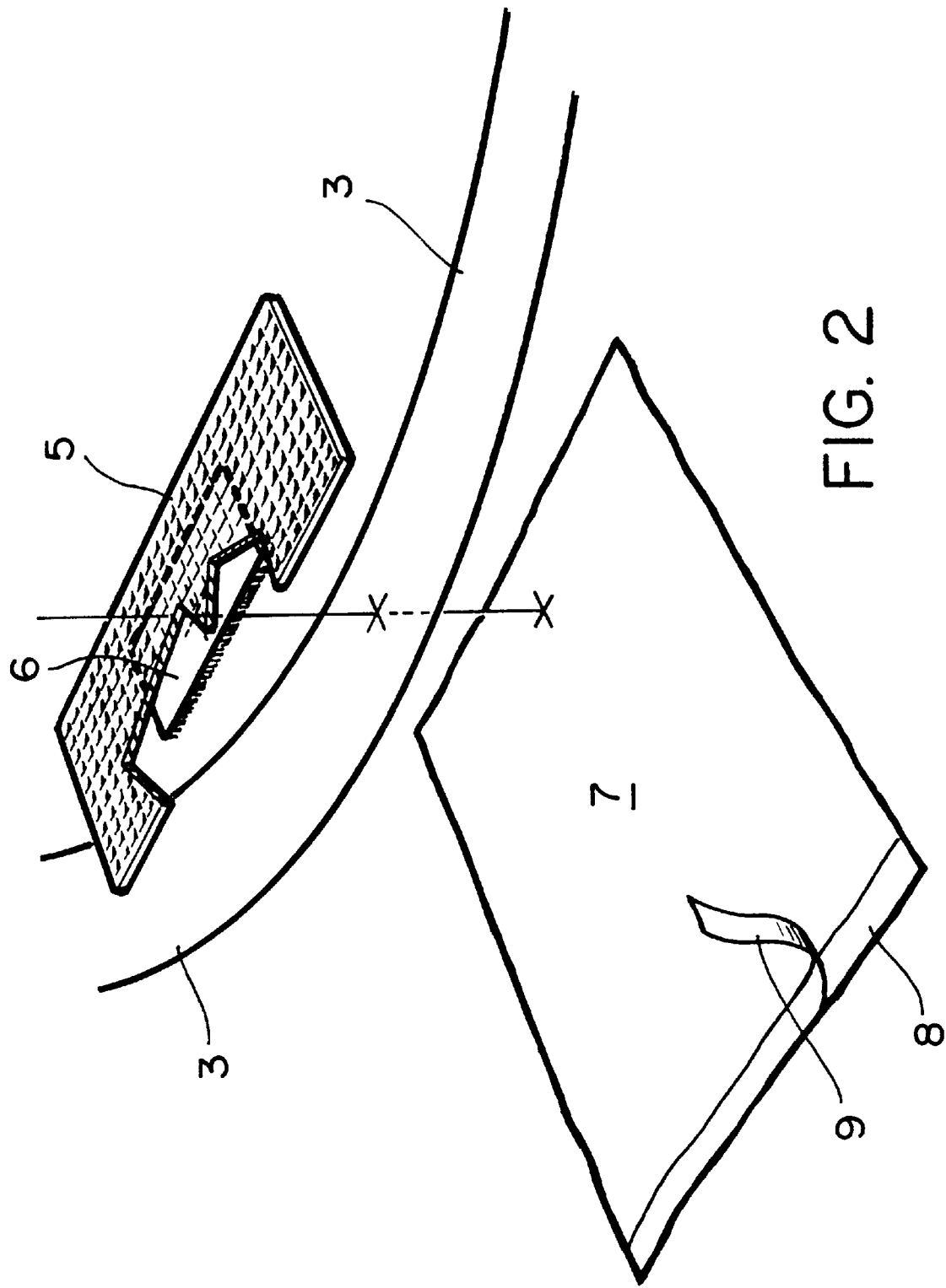
FIG. 2 is an exploded view of the support package.

The support package 4 is shown in FIG. 2 in an exploded view. Again the support band is shown at 3. One of the most important part of this invention is a semi-rigid but flexible open grid panel of plastic material 5. This material is similar to backing panels found in craft stores and used in embroidery. It is important that it is semi-rigid because, when in use, it will hold its shape but it also flexible enough so that it will adjust itself to the curvature of the body between the legs. Since it is a plastic material it can easily be cleaned and it is durable.

Figure 4:
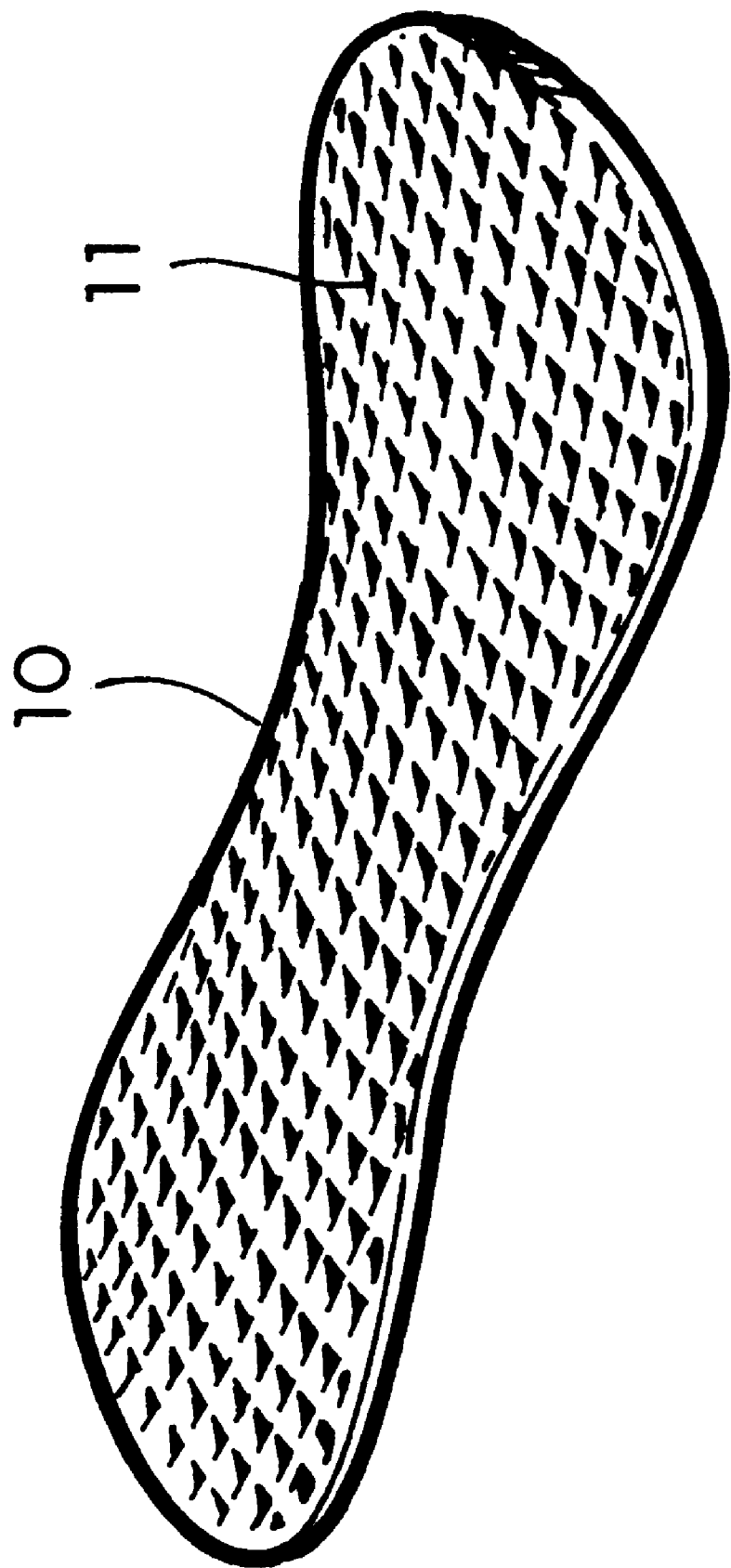
FIG. 4 shows a different shape of the basic support package.

Still referring to FIG. 4 a piece of male hook material is attached to the underside of the open grid panel 5 which will attach itself to any loops of the support band 3. The reason for the hook material is so that once the proper location of the support package has been determined, the hook material will ensure that the support package will stay in that location.

Still referring to FIG. 2 there is shown a padding material 7 which is wrapped around the open grid panel and around the support belt 3. once it is tightly wrapped around the above noted elements, the outer edge of the padding 7 is fastened to the underside of the wrapped padding by way of an adhesive strip 8. Just prior to fastening the protective paper strip is removed to expose the adhesive. Instead of a self-adhesive strip, a strip of male hook fasteners could be used which is attached to the edge of the padding 7 in a similar manner as at 8.

Figure 3:
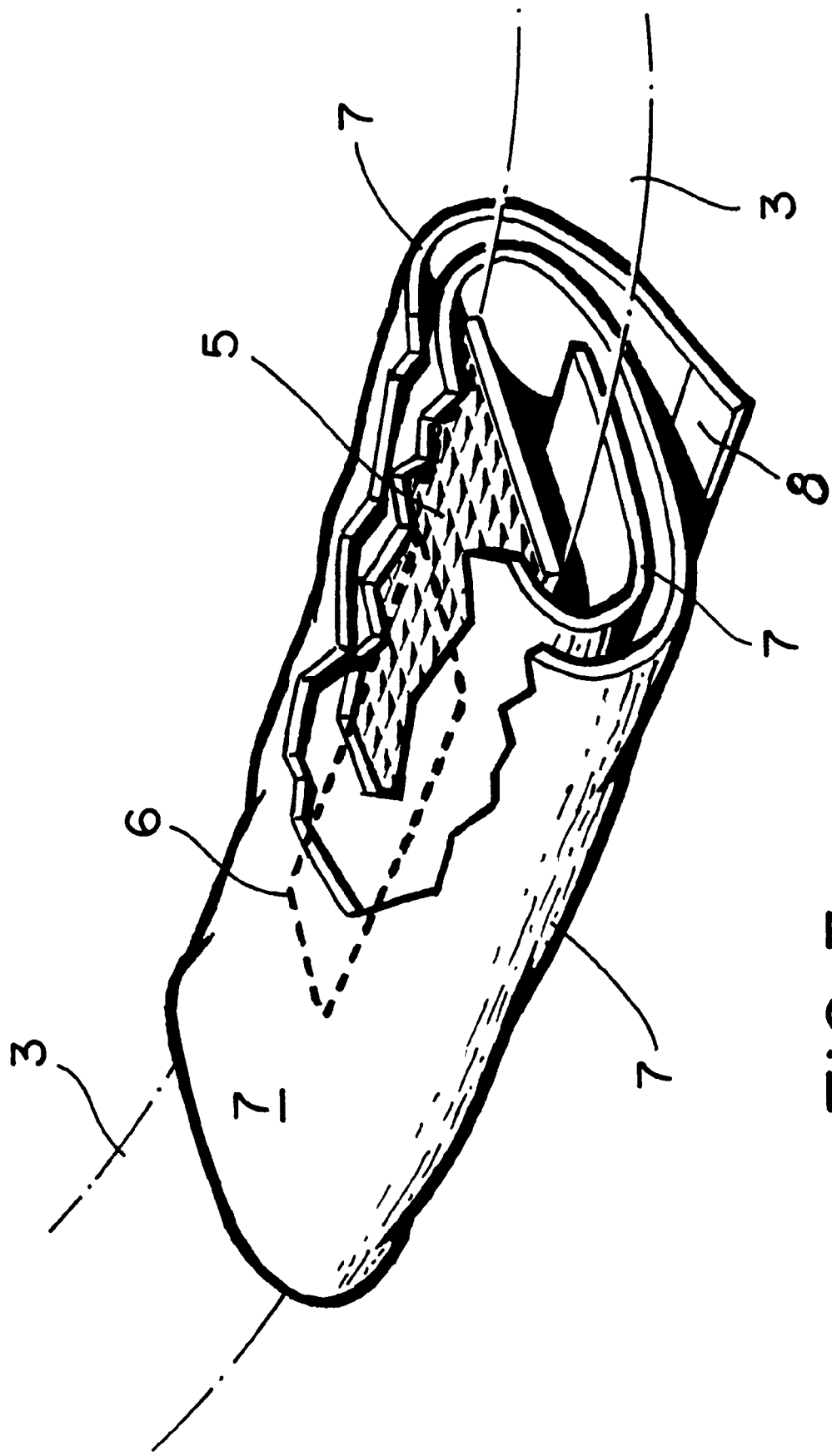
FIG. 3 shows the sandwich construction of the support package.

Referring now to FIG. 3, there is shown the sandwich construction of the just described method of assembly with regard to FIG. 2 and wherein like reference characters have been used for like elements. It can be seen that the padding 7 exhibits at least two layers on the side where contact is made with the body of a wearer while the adhesive edge 8 remains on the bottom of the support package 4 so that no comfort disturbing edges are in contact with any areas of the body of the person wearing the support garment.

Turning now to FIG. 4, there is shown a different shape for the open grid support panel. In certain circumstances it is desirable that the semi-rigid support panel be shaped in an hour-glass shape 10 so that it more comfortably fits between the legs of a wearer to minimize any chafing even though the padding 7 is tightly wrapped around the panel 10 which will somewhat cushion any rubbing or friction. At 11, there are shown, schematically the openings in the open grid panel 10.

For the padding itself a soft sheet of woven material could be used or a sheet of loose felt material or a sheet of gauze-like material.

What I claim is:

1. A support garment comprising a waist band and a support band to be placed between the legs of a person wearing said support garment, a support package placed approximately midway on said support band and thereby between the legs of a wearer, said support package includes a semi-rigid but flexible open grid panel of plastic material which is in contact with an upper surface of said support band and a sheet of soft padding wrapped around said panel and said support band and means for fastening an edge of said sheet to said sheet.

2. The support garment according to claim 1, wherein said waistband consists of elastic material.

3. The support garment according to claim 1, wherein said waistband has means for adjusting the size of its girth.

4. The support garment according to claim 1 including means for fastening said panel to a location on an upper surface of said support band.

5. The support garment according to claim 1 including means for detachably fastening said support band to said waistband.

6. The support garment according to claim 1, wherein said panel has a rectangular shape.

7. The support garment according to claim 1, wherein said panel has the shape of an hour-glass.

* * * * *